US012605077B2

(12) United States Patent
Chen et al.

(10) Patent No.: US 12,605,077 B2
(45) Date of Patent: Apr. 21, 2026

(54) PHOTOPLETHYSMOGRAM SYSTEM AND METHOD

(71) Applicant: PRANAQ PTE. LTD., Taipei City (TW)

(72) Inventors: Cheng-Yao Chen, Taipei City (TW); Uei-Ming Jow, Taipei City (TW); Chih-Wei Hsu, Taipei City (TW)

(73) Assignee: PRANAQ PTE. LTD., Taipei City (TW)

( * ) Notice: Subject to any disclaimer, the term of this patent is extended or adjusted under 35 U.S.C. 154(b) by 327 days.

(21) Appl. No.: 18/237,898

(22) Filed: Aug. 25, 2023

(65) Prior Publication Data

US 2025/0064323 A1 Feb. 27, 2025

(51) Int. Cl.
| | |
|---|---|
| *A61B 5/0205* | (2006.01) |
| *A61B 5/024* | (2006.01) |
| *A61B 5/08* | (2006.01) |
| *A61B 5/1455* | (2006.01) |

(52) U.S. Cl.
CPC ........ *A61B 5/0205* (2013.01); *A61B 5/14552* (2013.01); *A61B 5/02405* (2013.01); *A61B 5/02416* (2013.01); *A61B 5/08* (2013.01)

(58) Field of Classification Search
CPC .............. A61B 5/0205; A61B 5/14552; A61B 5/02405; A61B 5/02416; A61B 5/08
See application file for complete search history.

(56) References Cited

U.S. PATENT DOCUMENTS

| | | | |
|---|---|---|---|
| 6,319,205 B1 | 11/2001 | Goor et al. | |
| 2014/0192177 A1* | 7/2014 | Bartula ................. | G06T 7/0016 |
| | | | 348/77 |
| 2019/0099125 A1 | 4/2019 | Schnall | |
| 2020/0015737 A1 | 1/2020 | Pee et al. | |
| 2020/0359971 A1* | 11/2020 | Zhao ...................... | G16H 40/63 |
| 2021/0059586 A1* | 3/2021 | Marriott .............. | A61B 5/7225 |
| 2021/0275043 A1* | 9/2021 | Ahmad ................. | A61B 5/1112 |
| 2021/0275090 A1* | 9/2021 | Papini ................... | A61B 5/681 |
| 2022/0211323 A1 | 7/2022 | Schnall | |

FOREIGN PATENT DOCUMENTS

| | | |
|---|---|---|
| EP | 3928689 A1 | 12/2021 |
| EP | 3973851 A1 | 3/2022 |
| WO | WO2022238492 A1 | 11/2022 |

* cited by examiner

*Primary Examiner* — Amanda L Steinberg
(74) *Attorney, Agent, or Firm* — Best & Flanagan LLP

(57) ABSTRACT

A photoplethysmogram system and method are disclosed. The system includes at least three light sources of different frequencies configured to emit light into a subject's skin. A PPG sensor detects the light from the multiple light sources after it has passed through the subject's skin and generates a PPG signal for each light source. A processor, communicatively coupled to the PPG sensor, receives the PPG signals and estimates physiological parameters from each PPG signal. The light sources may include a red light source, an infrared light source, and a green light source, with the green light source used for calibration in the measurement of blood oxygen saturation. The processor may dynamically perform amputation or imputation of the PPG signals based on the consistency of the signals from the different light sources. The physiological parameters may include respiratory effort and pulse rate and pulse rate variability.

12 Claims, 7 Drawing Sheets

Receive PPG signals from sensor — S310

Estimate respiratory effort from each PPG signal — S320

Identify segments of estimated respiratory effort that meet a quality criterion — S330

Retain identified segments for further processing — S340

Receive PPG signals from sensor —— S610

Determine pulse rate and pulse rate variability for each PPG signal —— S620

Blend results from two closest PPG signals to provide final output —— S630

PHOTOPLETHYSMOGRAM SYSTEM AND METHOD

BACKGROUND OF THE INVENTION

1. Field of the Invention

The present invention relates generally to the field of medical devices and, more particularly, to a photoplethysmogram system and method.

2. Description of the Prior Art

Photoplethysmography (PPG) is a non-invasive technology that measures changes in blood volume in the microvascular bed of tissue. It is commonly used in devices like pulse oximeters to measure oxygen saturation (SpO2), but it can also provide other valuable physiological information such as pulse rate, blood pressure, and respiratory rate. However, conventional Photoplethysmography systems typically use only two light sources of specific frequencies, most commonly red and infrared. These systems may not provide a comprehensive picture of blood flow in both the superficial and deeper vessels. Furthermore, the accuracy of these systems can be affected by various factors such as skin color, thickness, and other characteristics that might affect the absorption of light.

Another challenge with conventional Photoplethysmography systems is the estimation of respiratory effort, which is crucial for the detection of respiratory disorders like sleep apnea. The estimation of respiratory effort from PPG signals can be complex and prone to errors, especially when the signals are noisy or contain artifacts. Additionally, the signal quality of the PPG signals in conventional systems is typically unstable with motion and/or displacement, which may not be optimal for further analysis. A poor signal quality or missing sample may not provide sufficient detail and/or consistent results for the application.

Therefore, there is a need for an improved Photoplethysmography system and method that can address these challenges. As it can be seen, how to address these challenges becomes an important issue to a person having ordinary skill in the art.

SUMMARY OF THE INVENTION

The present invention relates to a photoplethysmogram (PPG) system and method for estimating physiological parameters. The system comprises at least three light sources of different frequencies configured to emit light into a subject's skin. A PPG sensor is configured to detect the light from the multiple light sources after it has passed through the subject's skin and to generate a PPG signal for each light source. A processor, communicatively coupled to the PPG sensor, is configured to receive the PPG signals from the PPG sensor and to estimate physiological parameters from each PPG signal.

In some embodiments, the at least three light sources include a red light source, an infrared light source, and a green light source. The green light source is used for calibration in the measurement of blood oxygen saturation, and the green PPG signal is used as a reference to normalize the information from the red and infrared PPG signals.

In other embodiments, the processor is further configured to dynamically perform amputation or imputation of the PPG signals based on the consistency of the signals from the different light sources. The physiological parameters may include respiratory effort, and the processor may be further configured to identify and retain segments of the estimated respiratory effort that meet a quality criterion, to generate an event list for each PPG signal, and to combine the estimated respiratory effort from the different PPG signals using a fusion algorithm. The fusion algorithm may include at least one of an ensemble learning technique, a feature fusion technique, a decision fusion technique, and a data fusion technique.

In further embodiments, the processor is further configured to construct a final respiratory waveform by fusion of the respiratory effort estimated from the PPG signals from the three light sources, taking wavelength penetration into account, and to determine the final respiratory effort events from the event lists of the three PPG signals.

In yet other embodiments, the physiological parameters include pulse rate and pulse rate variability, and the processor is further configured to determine the pulse rate and pulse rate variability for each PPG signal, and to blend the results from the two closest PPG signals to provide a final output of pulse rate and pulse rate variability.

The invention also encompasses a photoplethysmogram method that includes emitting light into a subject's skin using at least three light sources of different frequencies, detecting the light from the multiple light sources after it has passed through the subject's skin and generating a PPG signal for each light source, and estimating physiological parameters from each PPG signal using a processor. The method may further include dynamically performing amputation or imputation of the PPG signals, identifying and retaining segments of the estimated respiratory effort, generating an event list for each PPG signal, combining the estimated respiratory effort from the different PPG signals using a fusion algorithm, constructing a final respiratory waveform, and determining the pulse rate and pulse rate variability for each PPG signal.

Other and further features, advantages, and benefits of the invention will become apparent in the following description taken in conjunction with the following drawings. It is to be understood that the foregoing general description and following detailed description are exemplary and explanatory but are not to be restrictive of the invention. The accompanying drawings are incorporated in and constitute a part of this application and, together with the description, serve to explain the principles of the invention in general terms. Like numerals refer to like parts throughout the disclosure.

BRIEF DESCRIPTION OF THE DRAWINGS

The objects, spirits, and advantages of the preferred embodiments of the present invention will be readily understood by the accompanying drawings and detailed descriptions, wherein.

DETAILED DESCRIPTION OF THE INVENTION

Figure 1:
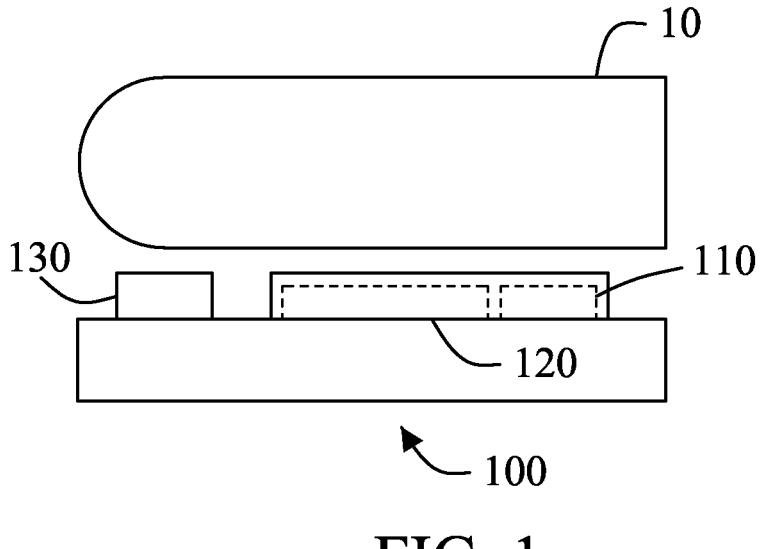
FIG. 1 shows an overview of a photoplethysmogram system of an embodiment of the present invention.

Please refer to FIG. 1. FIG. 1 shows a photoplethysmogram system 100 of an embodiment of the present invention. The photoplethysmogram system 100 includes at least three light sources 110 of different frequencies, a PPG sensor 120, and a processor 130. The light sources 110 are configured to emit light into a subject's skin. In some embodiments, the light sources 110 may include a red light source, an infrared light source, and a green light source. However, the invention is not limited to these specific frequencies, and other light sources of different frequencies can also be used. The use of multiple light sources of different frequencies allows for a more comprehensive measurement of blood flow in both the superficial and deeper vessels of the skin.

The PPG sensor 120 is configured to detect the light from the light sources 110 after it has passed through the subject's skin (e.g., the patient's finger 10). The PPG sensor 120 generates a photoplethysmogram (PPG) signal for each light source. These PPG signals represent the changes in blood volume in the microvascular bed of the tissue, which can provide valuable physiological information or physiological parameters, such as blood oxygen saturation, pulse rate and pulse rate variability, and respiratory effort. The processor 130 is communicatively coupled to the PPG sensor 120. In one embodiment, the processor 130 receives the PPG signals from the PPG sensor 120 and estimates respiratory effort from each PPG signal. The estimation of respiratory effort is important for the detection of respiratory disorders like sleep apnea. The processor 130 can use various algorithms and techniques to estimate respiratory effort from the PPG signals, as will be described in more detail in the subsequent embodiments.

In this way, the photoplethysmogram system 100 provides a non-invasive method for measuring physiological parameters and detecting respiratory disorders. The use of multiple light sources of different frequencies, along with the dynamic amputation or imputation and the use of a fusion algorithm, allows for a more accurate and reliable estimation of physiological parameters.

The above description provides a basic understanding of the photoplethysmogram system. The following embodiments will further describe the specific features and functionalities of the system in more detail.

Figure 2:
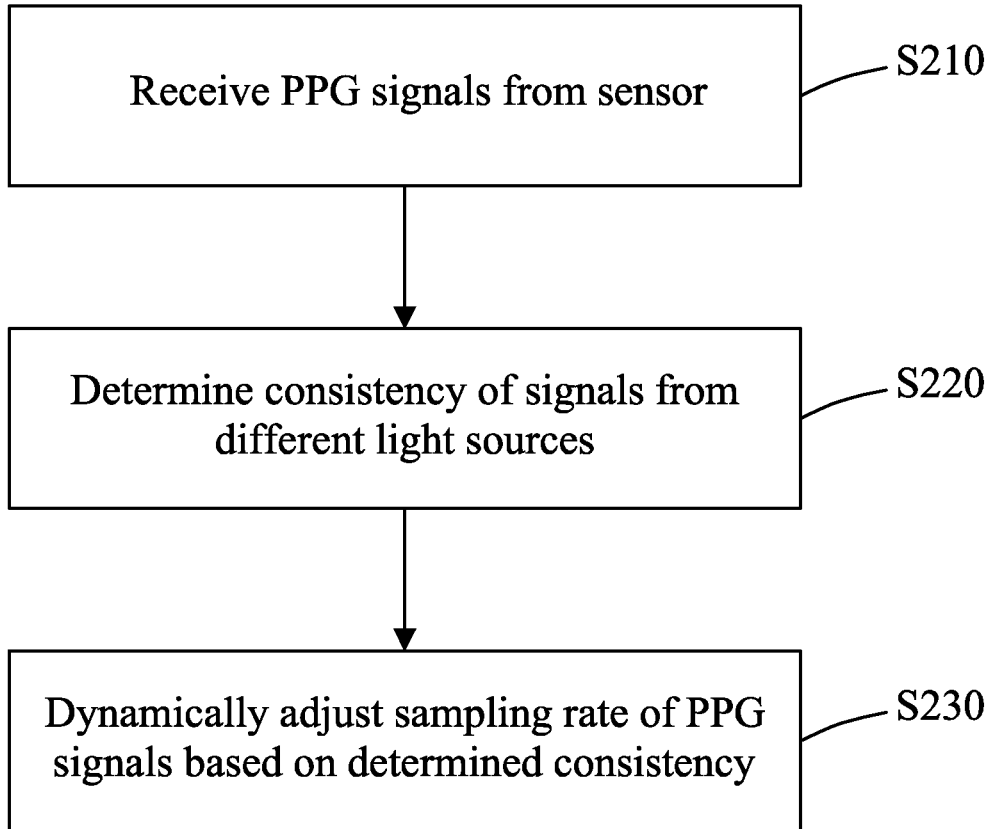
FIG. 2 shows a flowchart illustrates the process of dynamically performing amputation or imputation of the photoplethysmogram (PPG) signals in the photoplethysmogram system.

Please refer to FIG. 1 and FIG. 2. FIG. 2 shows a flowchart illustrates the process of dynamically performing amputation or imputation of the photoplethysmogram (PPG) signals in the photoplethysmogram system 100. In step S210, the processor 130 receives the PPG signals from the PPG sensor 120. These signals are generated by the PPG sensor 120 based on the light from the different light sources 110 that has passed through the subject's skin. In step S220, the processor 130 determines the consistency of the signals from the different light sources 110. The consistency of the signals can be determined by comparing the PPG signals from the different light sources 110. In step S230, based on the determined consistency, the processor 130 dynamically perform amputation or imputation of the PPG signals. If the signals are very consistent, indicating that the measurements are reliable, the processor 130 will generate a high confidence indicator for further analysis. On the other hand, if the signals are less consistent, indicating that there are some disturbances or artifacts in the signals, the processor 130 might perform amputation or imputation based on a pre-trained regression-based model the unstable channel.

In the embodiment, "amputation" and "imputation" refer to two different operations performed on the PPG signals based on the evaluation of signal quality. "Amputation" refers to the process where if all channels (or a majority of the channels) have a signal quality that falls below a set poor signal quality threshold, or if any channel has a signal quality below the poor signal quality threshold and the cumulative poor signal quality indicator exceeds a set percentage threshold, the current poor quality data point is removed from the signal. Concurrently, the cumulative poor signal quality indicator is increased. The sentence "the cumulative poor signal quality indicator is increased" refers to the process where, with every instance of "amputation" (i.e., removal of the current poor quality data point), a counter or indicator is increased by a unit or a specific value. This cumulative poor signal quality indicator is used to track and record how many data points in the PPG signal are considered of poor quality and have been removed. This indicator can help the system understand the overall quality situation of the PPG signal and can be used to determine whether further signal processing or adjustment is warranted. For instance, if this cumulative poor signal quality indicator exceeds a set threshold, the system may decide to perform a more thorough cleanup of the PPG signal, or alert the user to change the measurement conditions to obtain a better signal quality.

"Imputation" refers to the process where if the above conditions are not met, i.e., when the signal quality has not reached the level of poor signal quality, the current poor quality data point is adjusted based on a pre-calibrated regression-based lookup table. This adjustment could be based on statistical analysis of the signal or predictions from a machine learning model, with the aim of improving the quality of the signal.

In summary, these "amputation" and "imputation" strategies aim to improve the quality of the PPG signals in situations where signal quality is poor, by removing or adjusting poor quality data points. This, in turn, enhances the accuracy of physiological parameter estimation.

The dynamic amputation or imputation in the photoplethysmogram system 100 is a key feature that enhances the system's adaptability and accuracy under varying conditions. This adaptability is particularly significant in relation to the use of different wavelength light sources 110. In the embodiment, the photoplethysmogram system 100 uses at least three light sources 110 of different frequencies to emit light into a subject's skin. The PPG sensor 120 detects the light after it has passed through the subject's skin and generates a PPG signal for each light source. The processor 130 then receives these PPG signals and estimates the physiological parameters, e.g. respiratory effort, from each PPG signal.

The dynamic amputation or imputation is implemented based on the consistency of these signals from the different light sources 110. For instance, when the subject is at rest and the signals from the different light sources 110 are likely to be consistent, the processor 130 can generate a high confidence indicator for later analysis. This approach allows the system to rely more on the detailed information about the blood flow, thereby enhancing the accuracy of the physiological parameters estimation. Conversely, in situations where the subject is moving or when there are other disturbances, the signals from the different light sources 110 may vary in consistency. In these scenarios, the processor 130 can employ an amputation or imputation mechanism to the inconsistent channel based on a regression-based model. This strategy helps to reduce the impact of the disturbances on the signal and ensures the reliability of the measurements, despite the less stable conditions.

In essence, the dynamic amputation or imputation mechanism allows the photoplethysmogram system 100 to effectively handle the variability introduced by the use of different wavelength light sources 110 and varying conditions. This adaptability is crucial in ensuring the accuracy and reliability of the physiological parameters estimation, making it a significant feature of the photoplethysmogram system 100.

Figure 3:
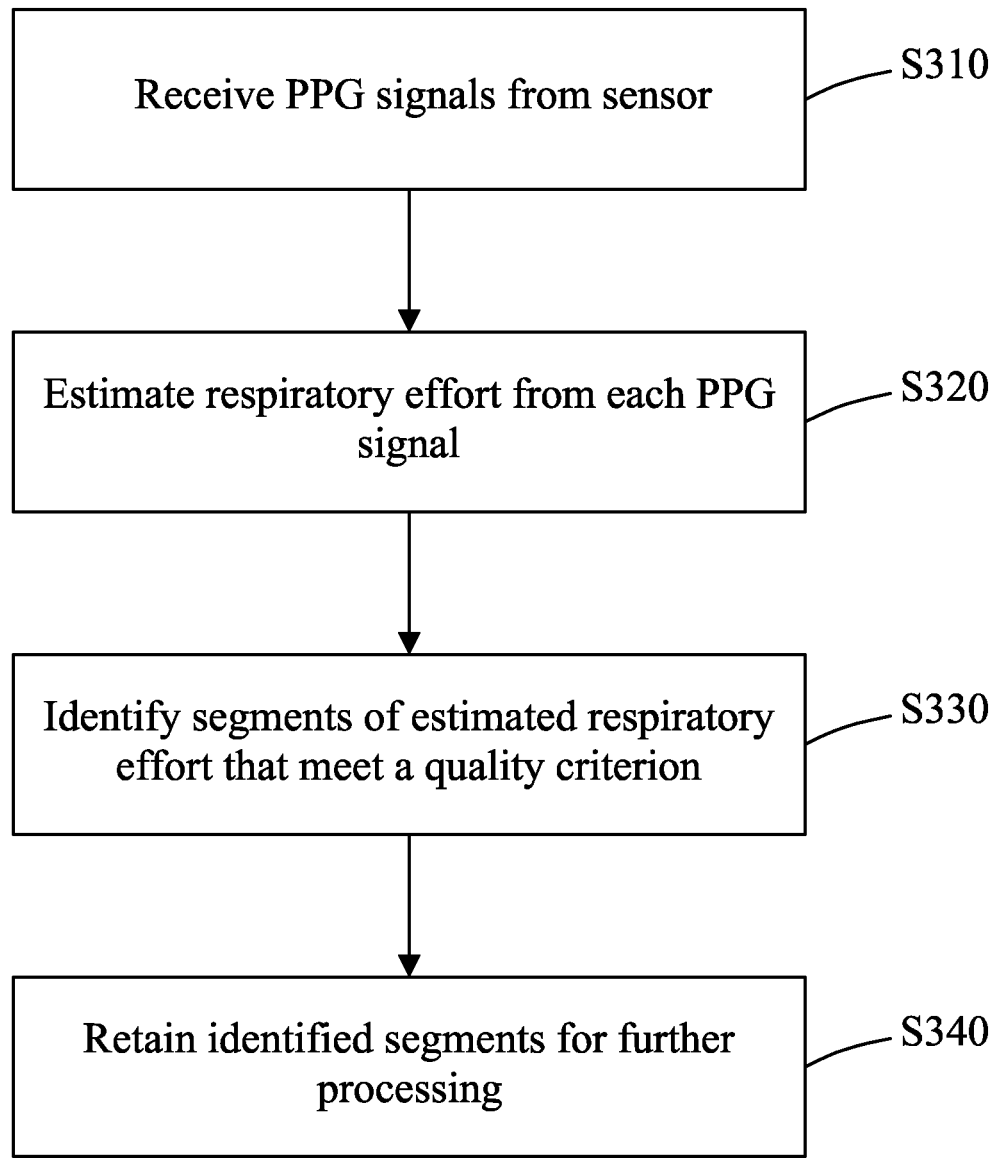
FIG. 3 shows a flowchart illustrating the process of identifying and retaining segments of the estimated respiratory effort in the photoplethysmogram system.

Please refer to FIG. 1 and FIG. 3. FIG. 3 shows a flowchart illustrating the process of identifying and retaining segments of the estimated respiratory effort in the photoplethysmogram system 100. In step S310, the processor 130 receives the PPG signals from the PPG sensor 120. These signals are generated by the PPG sensor 120 based on the light from the different light sources 110 that has passed through the subject's skin. In step S320, the processor 130 estimates the respiratory effort from each PPG signal. This estimation can be based on various factors, such as the amplitude and wavelength of the PPG signals, and can involve various signal processing techniques, such as filtering and spectral analysis.

In step S330, the processor 130 identifies segments of the estimated respiratory effort that meet a quality criterion. The quality criterion can be based on various factors, such as the signal-to-noise ratio, the consistency of the estimated respiratory effort, and the correlation with other physiological parameters. For example, a segment might be considered to meet the quality criterion if the signal-to-noise ratio is above a certain threshold, if the estimated respiratory effort is consistent over a certain period of time, or if the estimated respiratory effort correlates well with other physiological parameters, such as the pulse rate or the blood oxygen saturation.

In step S340, the processor 130 retains the identified segments of the estimated respiratory effort for further processing. These segments can be used for various purposes, such as monitoring the subject's respiratory condition, diagnosing respiratory disorders, or guiding the treatment of respiratory disorders. The identification and retention of segments of the estimated respiratory effort that meet a quality criterion is an important feature of the photoplethysmogram system 100, as it ensures the reliability of the estimated respiratory effort and enhances the accuracy and usefulness of the respiratory information derived from the PPG signals.

Figure 4:
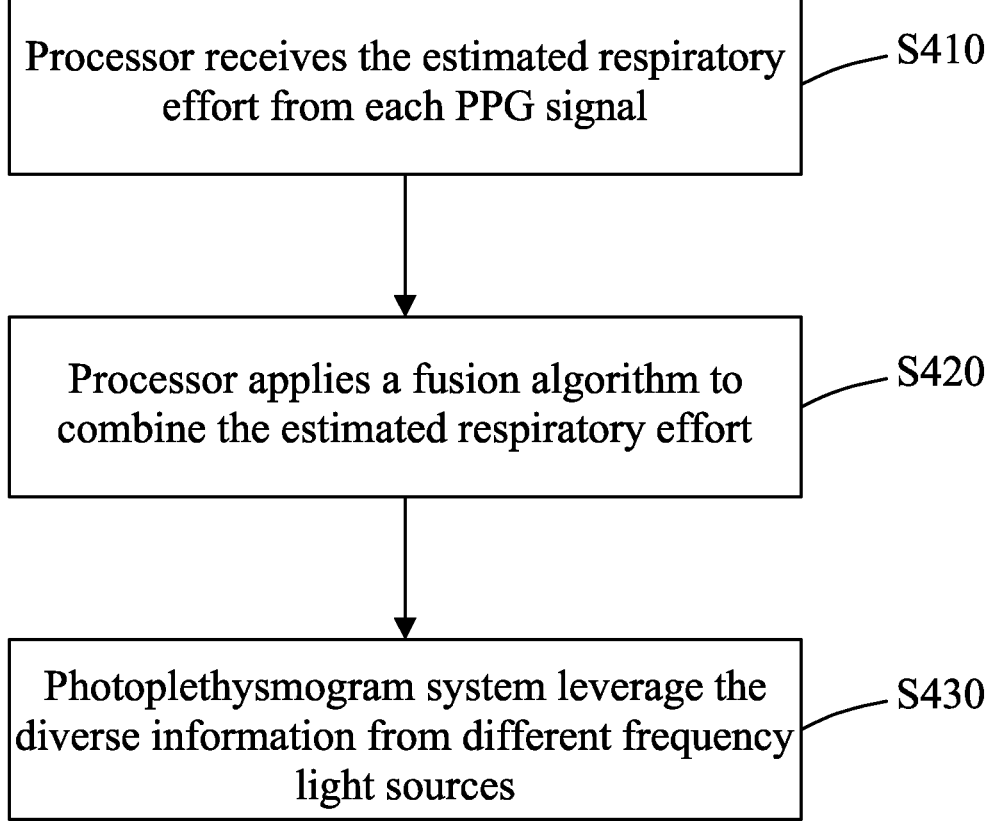
FIG. 4 shows a flowchart illustrating the process of combining the estimated respiratory effort from the different PPG signals using a fusion algorithm in the photoplethysmogram system.

Please refer to FIG. 1 and FIG. 4. FIG. 4 shows a flowchart illustrating the process of combining the estimated respiratory effort from the different PPG signals using a fusion algorithm in the photoplethysmogram system 100. In step S410, the processor 130 receives the estimated respiratory effort from each PPG signal. These estimates are generated by the processor 130 based on the PPG signals from the PPG sensor 120. In step S420, the processor 130 applies a fusion algorithm to combine the estimated respiratory effort from the different PPG signals. The fusion algorithm can include at least one of an ensemble learning technique, a feature fusion technique, a decision fusion technique, and a data fusion technique. In step S430, the photoplethysmogram system 100 can effectively leverage the diverse information provided by the different wavelength light sources.

An ensemble learning technique can involve combining the outputs of multiple models to produce a final output. This can help to improve the robustness and accuracy of the estimated respiratory effort by leveraging the strengths of different models and mitigating their weaknesses. A feature fusion technique can involve combining the features extracted from the different PPG signals to produce a combined feature set. This can help to capture the complementary information contained in the different PPG signals and to enhance the representativeness of the features.

A decision fusion technique can involve combining the decisions made based on the different PPG signals to produce a final decision. This can help to improve the reliability of the decision by taking into account the consensus among the different decisions. A data fusion technique can involve combining the raw data from the different PPG signals to produce a combined data set. This can help to enhance the richness of the data and to increase the diversity of the information available for the estimation of the respiratory effort.

In some embodiment, the ensemble learning technique can be implemented as follows. First, the processor 130 receives the estimated respiratory effort from each PPG signal. These estimates are generated based on the PPG signals from the PPG sensor 120, each corresponding to a different wavelength light source. Then, the processor 130 applies an ensemble learning technique as part of the fusion algorithm. This involves the use of multiple models, each trained to estimate respiratory effort based on the PPG signal from a particular light source. Each model thus specializes in interpreting the signal from a specific light source, taking into account the unique characteristics and potential disturbances associated with that wavelength.

The outputs of these models are then combined to produce a final estimate of respiratory effort. This combination can be done in various ways, such as by taking a weighted average of the outputs, where the weights could be determined based on the reliability or confidence of each model's output. By using an ensemble of models, the photoplethysmogram system 100 can effectively leverage the diverse information provided by the different wavelength light sources. This approach helps to improve the robustness of the system against disturbances and enhances the accuracy of the respiratory effort estimation, making it a highly effective technique for the fusion of PPG signals in the photoplethysmogram system 100.

Figure 5:
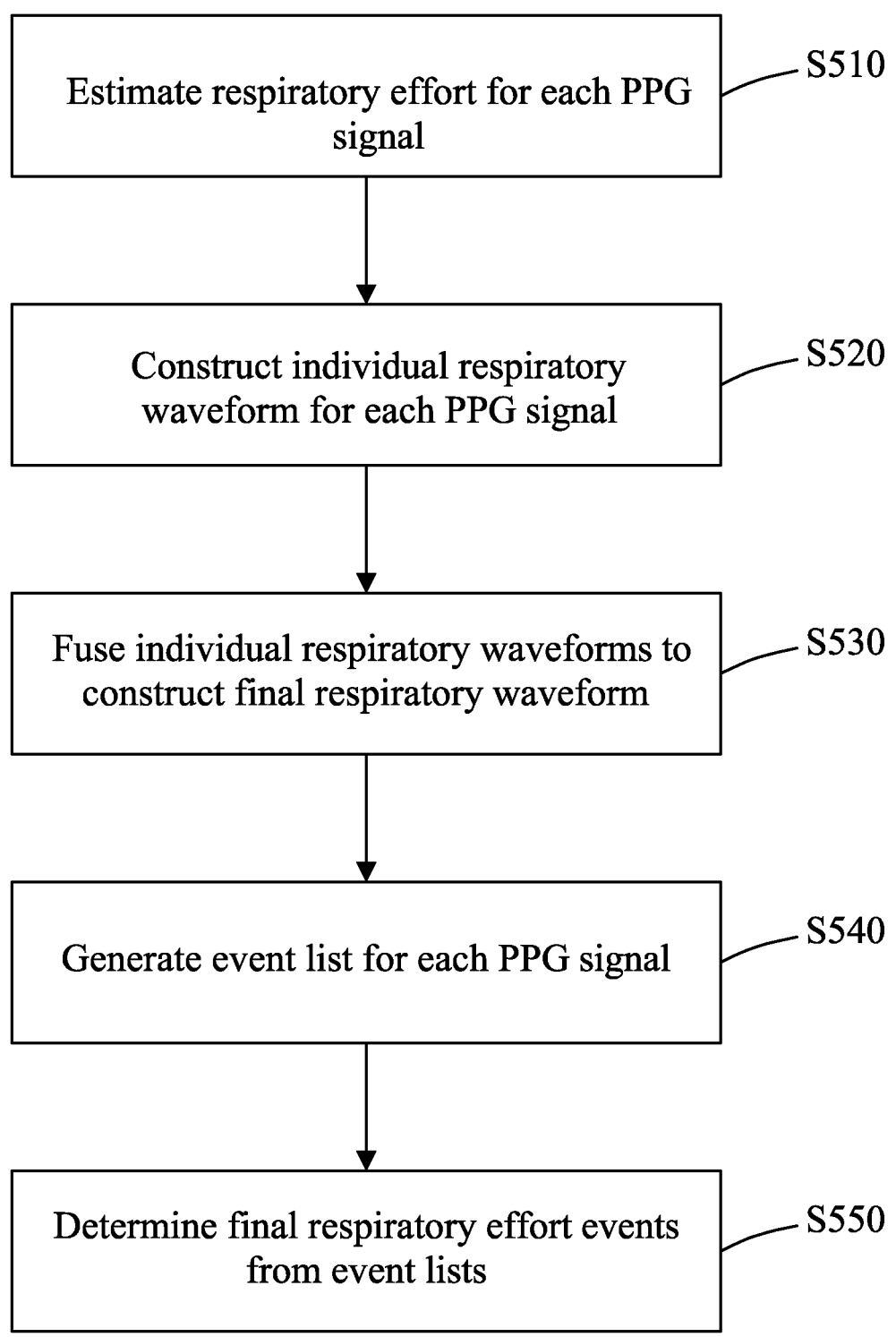
FIG. 5 shows a flowchart illustrating the process of constructing a final respiratory waveform and determining respiratory effort events in the photoplethysmogram system.

To provide a clearer explanation, please refer to FIG. 1 and FIG. 5. FIG. 5 shows a flowchart illustrating the process of constructing a final respiratory waveform and determining respiratory effort events in the photoplethysmogram system 100. In step S510, the processor 130 estimates the respiratory effort for each PPG signal. These signals are generated by the PPG sensor 110 based on the light from the different light sources 110a, 110b, and 110c that has passed through the subject's skin. In step S520, the processor 130 constructs an individual respiratory waveform for each PPG signal. This process involves converting the estimated respiratory effort into a waveform representation. The waveform for each PPG signal reflects the changes in respiratory effort over time.

In step S530, the processor 130 fuses the individual respiratory waveforms from the three PPG signals to construct a final respiratory waveform. This fusion process involves combining the individual waveforms in a way that takes into account the wavelength penetration of each light source. For example, the waveform from the infrared light source 110b, which has the deepest penetration, may be given more weight in the fusion process. In step S540, the processor 130 generates an event list for each PPG signal. Each event in the list corresponds to a significant event in the respiratory effort, such as the start of an inhalation or exhalation. In step S550, the processor 130 determines the final respiratory effort events from the event lists of the three PPG signals. This process involves combining the events from the three lists in a way that ensures the final list of events accurately reflects the respiratory effort of the subject.

This embodiment regarding FIG. 5 provides a comprehensive and accurate estimation of the respiratory effort by leveraging the information from multiple PPG signals and taking into account the wavelength penetration of each light source. The final respiratory waveform and list of respiratory effort events can be used for various applications, such as monitoring the respiratory health of a subject or diagnosing respiratory conditions.

Figure 6:
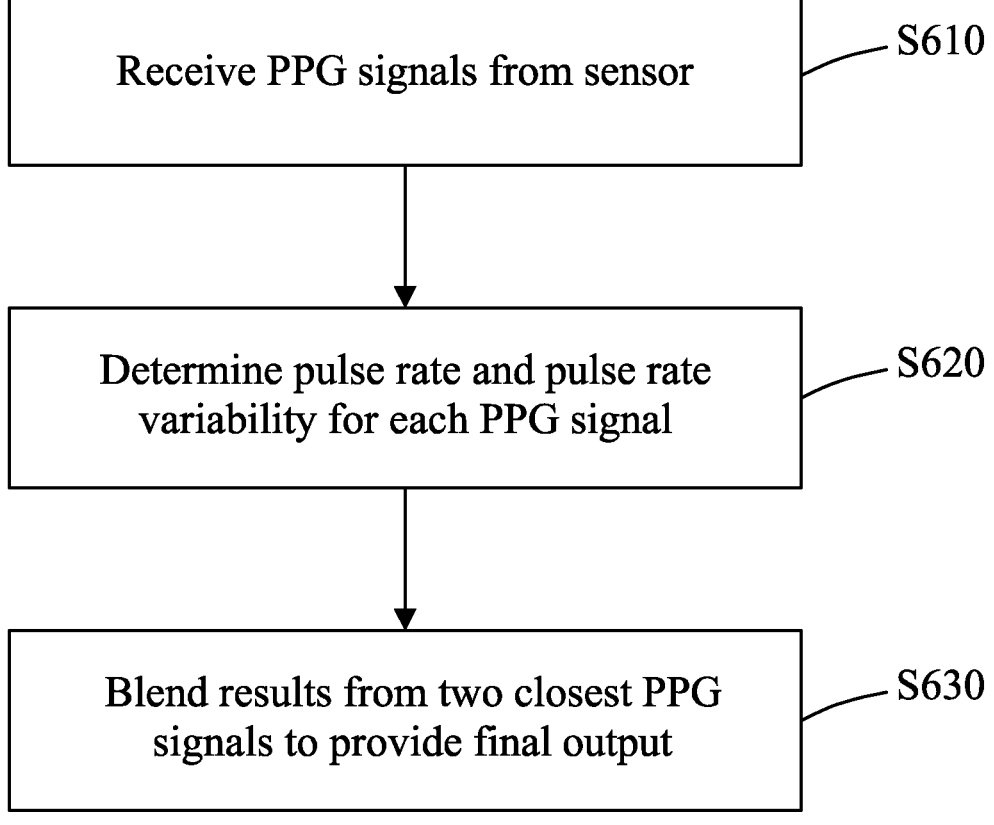
FIG. 6 shows a flowchart illustrating the process of determining pulse rate and pulse rate variability in the photoplethysmogram system.

In some embodiment, the processor 130 is further configured to determine the pulse rate and pulse rate variability for each PPG signal, and to blend the results from the two closest channel outputs to provide a final output of pulse rate and pulse rate variability. Please refer to FIG. 1 and FIG. 6. FIG. 6 shows a flowchart illustrating the process of determining pulse rate and pulse rate variability in the photoplethysmogram system.

In step S610, the processor 130 receives the PPG signals from the PPG sensor 120. These signals are generated by the PPG sensor 120 based on the light from the different light sources 110 that has passed through the subject's skin. In step S620, the processor 130 determines the pulse rate and pulse rate variability for each PPG signal. This can be achieved by applying peak detection to each PPG signal to identify the peaks that correspond to the heartbeats. The time intervals between these peaks can then be used to calculate the pulse rate (as the number of heart beats per minute) and the pulse rate variability (as the variation in the time intervals between heartbeats).

In step S630, the processor 130 blends the results from the two closest channel outputs to provide a final output of pulse rate and pulse rate variability. This blending process can be based on a weighted average, with higher weighting given to the channel that provides the most consistent and reliable results. For example, if the green channel provides the most consistent results, it may be given a higher weighting in the blending process.

This process allows the photoplethysmogram system 100 to provide accurate and reliable measurements of pulse rate and pulse rate variability, even in the presence of disturbances or artifacts in the PPG signals. It also allows the system to adapt to variations in the physiological conditions of the subject, such as changes in skin color, thickness, or blood flow.

Figure 7:
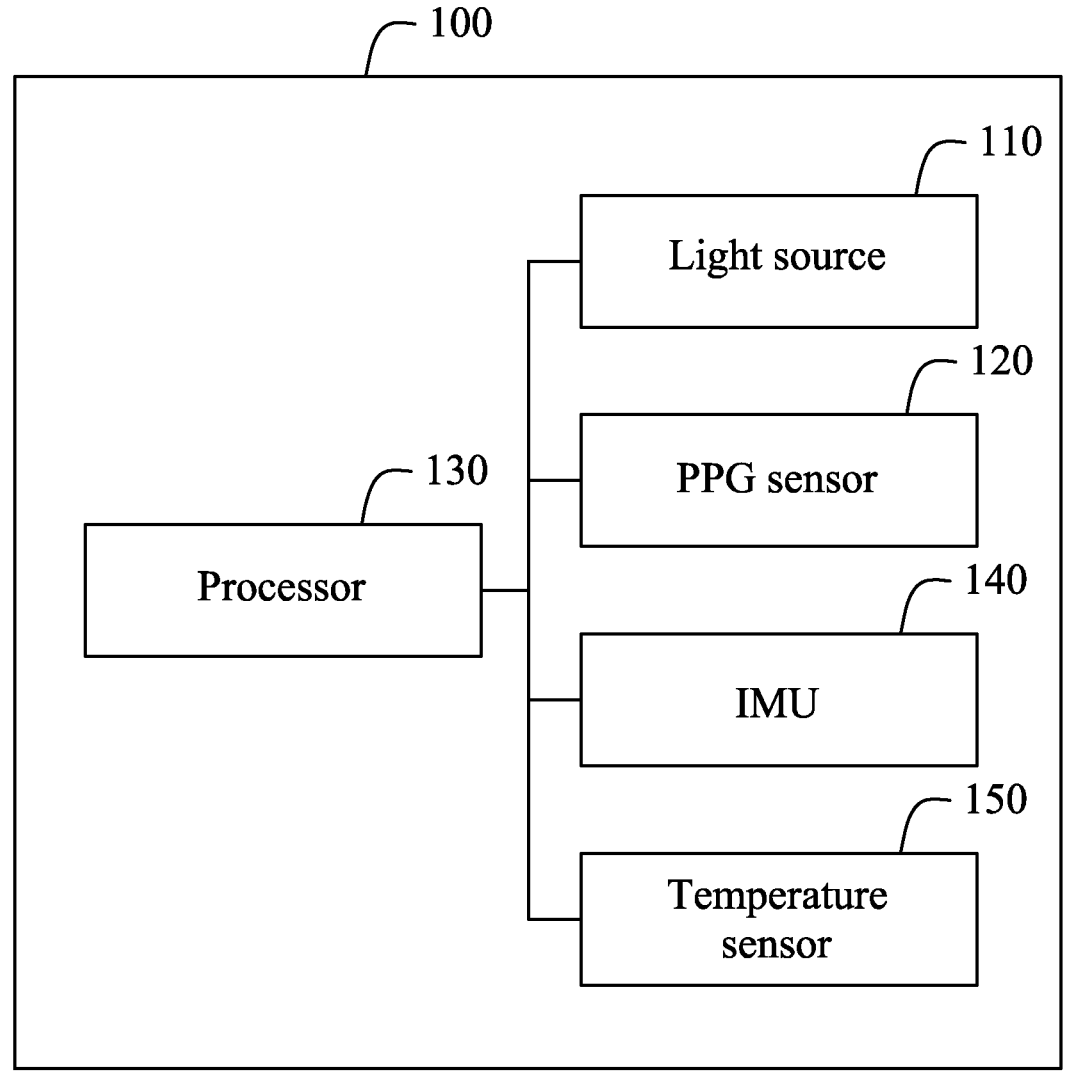
FIG. 7 shows a schematic diagram illustrates the use of the green light source for calibration in the measurement of blood oxygen saturation (SpO2) in the photoplethysmogram system.

Please refer to FIG. 7. FIG. 7 shows a schematic diagram illustrates the use of the green light source for calibration in the measurement of blood oxygen saturation (SpO2) in the photoplethysmogram system. In the photoplethysmogram system 200, the light sources 110 include a green light source, among others. In the embodiments, the red and infrared light sources are used to calculate blood oxygen saturation (SpO2). The red and infrared light are absorbed differently by oxygenated and deoxygenated hemoglobin, allowing the calculation of SpO2 based on the ratio of the absorption of these two light sources. The green light source in the embodiment is used for calibration in the measurement of SpO2. The green light source emits green light into the subject's skin, and the PPG sensor 120 detects the green light after it has passed through the subject's skin and generates a green PPG signal.

The processor 130 receives the green PPG signal from the PPG sensor 120 and uses it for calibration in the measurement of SpO2. The calibration process can involve adjusting the measurement of SpO2 based on the green PPG signal to account for variations in skin color, thickness, or other characteristics that might affect the absorption of light. For example, the processor 130 can determine a correction factor based on the green PPG signal and apply the correction factor to the measurement of SpO2. The correction factor can be determined based on a comparison of the green PPG signal with a reference signal or based on a model that relates the green PPG signal to the variations in skin color, thickness, or other characteristics. The use of the green light source for calibration in the measurement of SpO2 is a significant feature of the photoplethysmogram system 200, as it allows the system to account for the variations in skin color, thickness, or other characteristics and to enhance the accuracy of the measurement of SpO2.

In addition to the use of the green light source for calibration, the photoplethysmogram system 200 can also utilize other sensors, such as an inertial measurement unit (IMU) 140 and a temperature sensor 150, to further enhance the accuracy of the measurements. The inertial measurement unit 140 can provide information about the motion and orientation of the subject. This information can be used by the processor 130 to adjust the PPG signals and the estimated respiratory effort to account for the effects of the subject's movements. For example, the processor 130 can apply a correction factor to the PPG signals based on the data from the inertial measurement unit 140 to reduce the impact of motion artifacts. This can be particularly important in situations where the subject is moving, as the movements can cause disturbances in the PPG signals and affect the accuracy of the estimated respiratory effort.

The temperature sensor 150 can provide information about the temperature of the subject's skin. This information can be used by the processor 130 to adjust the PPG signals and the estimated respiratory effort to account for the effects of temperature variations. For example, the processor 130 can apply a correction factor to the PPG signals based on the data from the temperature sensor to account for the effects of temperature on the absorption of light. This can be particularly important in situations where there are significant temperature variations, as these variations can affect the absorption of light and thus the accuracy of the PPG signals and the estimated respiratory effort.

By using these additional sensors for calibration, the photoplethysmogram system 200 can further enhance the accuracy and reliability of the measurements. This multi-sensor approach allows the system to account for a wide range of factors that can affect the PPG signals and the estimated respiratory effort, making it a highly versatile and robust system for the estimation of respiratory effort.

In conclusion, the present invention provides a photoplethysmogram (PPG) system and method that offer enhanced accuracy and reliability in estimating physiological parameters. The system utilizes at least three light sources of different frequencies, a PPG sensor, and a processor. The processor is configured to dynamically perform amputation or imputation of the PPG signals based on their consistency, and to estimate physiological parameters such as respiratory effort, pulse rate, and pulse rate variability from each PPG signal. The processor also employs a fusion algorithm to combine the estimated respiratory effort from the different PPG signals, and constructs a final respiratory waveform taking wavelength penetration into account. Furthermore, the processor determines the pulse rate and pulse rate variability for each PPG signal and blends the results from the two closest PPG signals to provide a final output.

The method of the present invention includes steps that correspond to the functionalities of the system components, providing a comprehensive approach to physiological parameter estimation.

The described system and method offer significant improvements in the field of physiological monitoring, providing a more accurate and reliable means of estimating key physiological parameters. This invention has the potential to greatly enhance the quality and effectiveness of health monitoring in various settings, from clinical to personal health applications.

While the embodiments have been described in detail, it should be understood that various changes, substitutions, and alterations could be made hereto without departing from the spirit and scope of the invention. For example, the specific types of light sources, the specific fusion algorithm, and the specific quality criterion can be varied depending on the specific application or requirements. Therefore, the described embodiments are to be considered as illustrative and not restrictive, and the invention is not to be limited to the details given herein but may be modified within the scope of the appended claims.

What is claimed is:

1. A photoplethysmogram system, comprising:
at least three light sources of different wavelengths configured to emit light into a subject's skin, the light sources including at least a red light source, an infrared light source, and a green light source;
a PPG sensor configured to detect the light from the multiple light sources after it has passed through the subject's skin and to generate, for each light source, a respective PPG signal; and
a processor communicatively coupled to the PPG sensor;
wherein the processor is configured to:
(a) for each PPG signal, estimate a first respiratory-effort signal from the PPG signal;
(b) for each time sample, determine a signal-quality value for each of the PPG signals based on a consistency of the PPG signals across the different wavelengths;
(c) maintain a cumulative poor-quality indicator, and when all of the signal-quality values, or a majority of the signal-quality values, are below a poor-quality threshold, or when any one of the signal-quality values is below the poor-quality threshold and the cumulative poor-quality indicator exceeds a predetermined percentage threshold, amputate the current time sample from the PPG signals and increase the cumulative poor-quality indicator; and
otherwise, when the signal-quality value of a particular PPG signal is below the poor-quality threshold, impute a value of the particular PPG signal at the current time sample based on a regression-based lookup table that uses one or more of the other PPG signals as input;
(d) after the amputation or imputation, re-estimate, for each PPG signal, a second respiratory-effort signal;

(e) for each PPG signal, identify segments of the second respiratory-effort signal that satisfy a quality criterion and generate a respiratory-effort event list for the PPG signal; and
(f) apply a fusion algorithm to the second respiratory-effort signals from the different wavelengths to construct a final respiratory waveform, the fusion algorithm assigning different weights to the second respiratory-effort signals according to wavelength-dependent penetration depth in tissue, and determine final respiratory-effort events from the respiratory-effort event lists.

2. The photoplethysmogram system of claim 1, wherein the processor is further configured to use a PPG signal associated with the green light source to normalize information contained in PPG signals associated with the red light source and the infrared light source.

3. The photoplethysmogram system of claim 1, wherein the fusion algorithm comprises at least one of an ensemble learning technique, a feature fusion technique, a decision fusion technique, and a data fusion technique.

4. The photoplethysmogram system of claim 1, wherein the processor is further configured to:
determine a pulse rate and a pulse rate variability for each PPG signal; and
blend the pulse rate and the pulse rate variability determined for two of the PPG signals whose pulse rate values are closest to each other to provide a final output of pulse rate and pulse rate variability.

5. The photoplethysmogram system of claim 1, further comprising an inertial measurement unit configured to sense motion of the subject, wherein the processor is configured to adjust at least one of the signal-quality value, the cumulative poor-quality indicator, and the respiratory-effort signals based on motion information from the inertial measurement unit to reduce an impact of motion artifacts.

6. The photoplethysmogram system of claim 1, further comprising a temperature sensor configured to measure a skin temperature of the subject, wherein the processor is configured to adjust at least one of the PPG signals and the respiratory-effort signals based on the measured temperature to improve an accuracy of the PPG signals and of the estimated respiratory effort.

7. A photoplethysmogram method, comprising:
emitting light into a subject's skin using at least three light sources of different wavelengths including at least a red light source, an infrared light source, and a green light source;
detecting the light from the multiple light sources after it has passed through the subject's skin and generating, for each light source, a respective PPG signal; and
by a processor;
(a) for each PPG signal, estimate a first respiratory-effort signal from the PPG signal;
(b) for each time sample, determine a signal-quality value for each of the PPG signals based on a consistency of the PPG signals across the different wavelengths, and updating a cumulative poor-quality indicator;
(c) when all of the signal-quality values, or a majority of the signal-quality values, are below a poor-quality threshold, or when any one of the signal-quality values is below the poor-quality threshold and the cumulative poor-quality indicator exceeds a predetermined percentage threshold, amputating the current time sample from the PPG signals and increasing the cumulative poor-quality indicator;

(d) otherwise, when the signal-quality value of a particular PPG signal is below the poor-quality threshold, imputing a value of the particular PPG signal at the current time sample based on a regression-based lookup table that uses one or more of the other PPG signals as input;

(e) after the amputating or imputing, re-estimating, for each PPG signal, a second respiratory-effort signal;

(f) for each PPG signal, identifying segments of the second respiratory-effort signal that satisfy a quality criterion, retaining the identified segments, and generating a respiratory-effort event list for the PPG signal; and (g) applying a fusion algorithm to the second respiratory-effort signals from the different wavelengths to construct a final respiratory waveform, the fusion algorithm assigning different weights to the second respiratory-effort signals according to wavelength-dependent penetration depth in tissue, and determining final respiratory-effort events from the respiratory-effort event lists.

8. The photoplethysmogram method of claim 7, further comprising using a PPG signal associated with the green light source to normalize information contained in PPG signals associated with the red light source and the infrared light source.

9. The photoplethysmogram method of claim 7, wherein the fusion algorithm includes at least one of an ensemble learning technique, a feature fusion technique, a decision fusion technique, and a data fusion technique.

10. The photoplethysmogram method of claim 7, further comprising:

determining a pulse rate and a pulse rate variability for each PPG signal; and blending the pulse rate and the pulse rate variability determined for two of the PPG signals whose pulse rate values are closest to each other to provide a final output of pulse rate and pulse rate variability.

11. The photoplethysmogram method of claim 7, further comprising:

receiving motion information from an inertial measurement unit; and adjusting at least one of the signal-quality values, the cumulative poor-quality indicator, and the respiratory-effort signals based on the motion information to reduce an impact of motion artifacts.

12. The photoplethysmogram method of claim 7, further comprising:

receiving temperature information from a temperature sensor; and adjusting at least one of the PPG signals and the respiratory-effort signals based on the temperature information to improve an accuracy of the PPG signals and of the estimated respiratory effort.

* * * * *